United States Patent [19]
Wetzel

[11] Patent Number: 5,225,167
[45] Date of Patent: Jul. 6, 1993

[54] ROOM AIR STERILIZER

[75] Inventor: Lawrence E. Wetzel, Cazenovia, N.Y.

[73] Assignee: Clestra Cleanroom Technology, Inc., N. Syracuse, N.Y.

[21] Appl. No.: 815,936

[22] Filed: Dec. 30, 1991

[51] Int. Cl.⁵ .......................... A61L 2/10; A61L 9/18
[52] U.S. Cl. ...................................... 422/121; 422/24; 55/279; 250/492.1
[58] Field of Search ...................... 422/24, 121, 186.3; 55/279; 250/453.11, 454.11, 455.11, 492.1

[56] References Cited

U.S. PATENT DOCUMENTS

| | | | |
|---|---|---|---|
| 3,846,072 | 11/1974 | Patterson | 55/279 X |
| 4,191,543 | 3/1980 | Peters | 422/122 X |
| 4,210,429 | 7/1980 | Goldstein | 422/121 X |
| 5,074,894 | 12/1991 | Nelson | 55/279 X |

Primary Examiner—Robert J. Warden
Assistant Examiner—Stephanie Blythe
Attorney, Agent, or Firm—Wall and Roehrig

[57] ABSTRACT

A room air sterilizer mounts on the wall of the room and traps airborne particulate in a HEPA filter. An ultraviolet germicidal lamp destroys any biocontamination on the trapped particulates. The sterilizer has an elongated vertical housing with a return air grille near or at its lower end and a HEPA filter assembly disposed at an outflow port at its upper end. The HEPA filter is preferably a quarter cylinder and the sterilizer lamp is situated to expose the inner or intake side of the filter to the sterilizing ultraviolet radiation. A prefilter can be situated ahead of the blowers for the sterilizer, and can have an associated ultraviolet sterilizer lamp.

10 Claims, 2 Drawing Sheets

ROOM AIR STERILIZER

BACKGROUND OF THE INVENTION

This invention relates to systems for purifying and sterilizing air in an enclosed room, and is more particularly directed to a room air sterilizer which may be mounted upon a wall of a room, for example, a hospital isolation room, a physician's office or a dentist's office. Due to recent outbreaks of highly infectious disease, such as tuberculosis, there has arisen a need for devices for filtering out particulates that carry diseasecausing microorganisms such as bacteria, virus, or spores. This need exists, for example, in places where the disease can easily spread from one person to another, such as in a prison hospital ward, an isolation room of a hospital or residence, or an office such as a dentist office, where there may be a high level of airborne particulates or aerosols that have become biocontaminants.

At present, so-called air "purifiers" can be of a media filter type or of an electrostatic type. However, neither type includes effective means to neutralize any biocontaminates. Ultraviolet sterilizer lamps are sometimes employed in health-care facilities, but these must be positioned somewhere in the room away from the patient, so that their radiation will not fall directly on a patient or another person. This limits their effectiveness, as they are generally out of the normal airflow path.

OBJECTS AND SUMMARY OF THE INVENTION

It is therefore an object of this invention to provide a room air sterilizer device which is suitable for use in hospitals, prisons, health care professional offices or residences to combat outbursts of diseases where there are airborne contaminants carried on particulates or aerosols.

It is another object of this invention to provide such a device which is capable of producing a positive overpressure or a negative underpressure, as need be, to control migration of biocontaminants into or out of a room.

It is a further object of this invention to provide a device which will filter out microscopic particles and then kill bacteria, spores, virus, disease causing microbes, or biological irritants such as pollen.

It is a still further object of this invention to provide an effective room air sterilizer which is simple to install and to maintain.

According to an aspect of this invention, the room sterilizer has a vertically disposed elongated housing with a lower end in which there is an intake port for drawing return air from near the floor of the room, and an upper end with an outflow port disposed at or near the room ceiling. A blower within the housing moves air in the direction from the intake port to the outflow port. A HEPA (high efficiency particulates air) filter assembly is positioned at the outflow port for trapping and holding any particulate and aerosols as the air passes through the filter from its inflow side to its outflow side. A germicidal ultraviolet lamp is situated within the housing at its upper end so as to expose the entire inflow side of the HEPA filter assembly to ultraviolet radiation at a wavelength that is suitable for destroying any microbial biocontamination which lands on the HEPA filter assembly. The housing can have a variable-height duct extension to allow adjustment of its height to fit the room size. The room air sterilizer also preferably has a prefilter disposed in the housing below the blower, with a second germicidal ultraviolet lamp disposed below the prefilter to expose its inflow side to the sterilizing ultraviolet radiation.

Preferably the HEPA filter assembly includes a quarter-cylindrical HEPA filter that has its axis disposed horizontally and substantially at the ceiling. This results in an airflow that is generally outward and downward from the sterilizer outflow port. A protective screen can be situated over the outside of the filter to block any direct line-of-sight path for the ultraviolet radiation.

An exhaust duct can be coupled to an exhaust port in the housing, positioned above the blower but below the HEPA filter assembly for exhausting air out of the room. This maintains a slight negative pressure within the room so that biocontaminants do not spread from the isolation room to other rooms in the same building. Alternatively or additionally, there can be an intake duct that is coupled to an intake port in the housing situated below the blower. This will bring additional, make-up air from outside the room into the housing to maintain a positive pressure within the room. This is useful if it is desired to prevent inflow of biocontaminated particulate into the room from other rooms in the building.

Preferably, the sterilizer will operate at an airflow rate of about 200-300 cfm. In a preferred mode, the ultraviolet sterilizer lamps are fluorescent lamps that emit radiation at about 254 nm, which is suitable for killing all microorganisms on small particles, i.e. 10 microns or less. The lamps are positioned to illuminate the "dirty" side of the filters. The fact that the upper HEPA filter is a quarter cylinder maximizes the UV exposure to the dirty or inflow side.

The above and many other objects, features, and advantages of this invention will be more fully apparent from the ensuing description of the preferred embodiment, which should be read in connection with the accompanying Drawing.

BRIEF DESCRIPTION OF A PREFERRED EMBODIMENT

Figure 1:
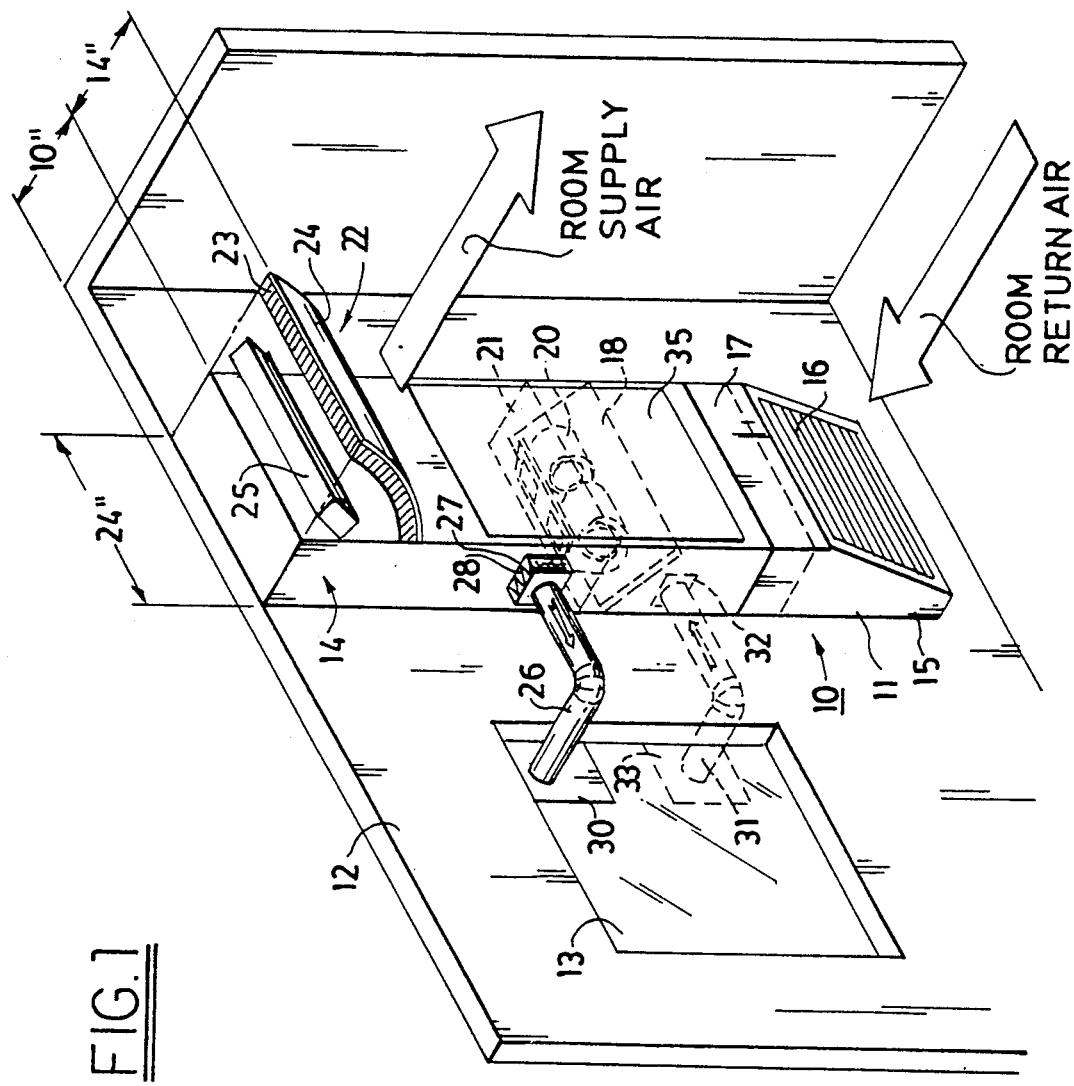
FIG. 1 is a perspective view of the room air sterilizer according to one preferred embodiment of this invention.
Figure 2:
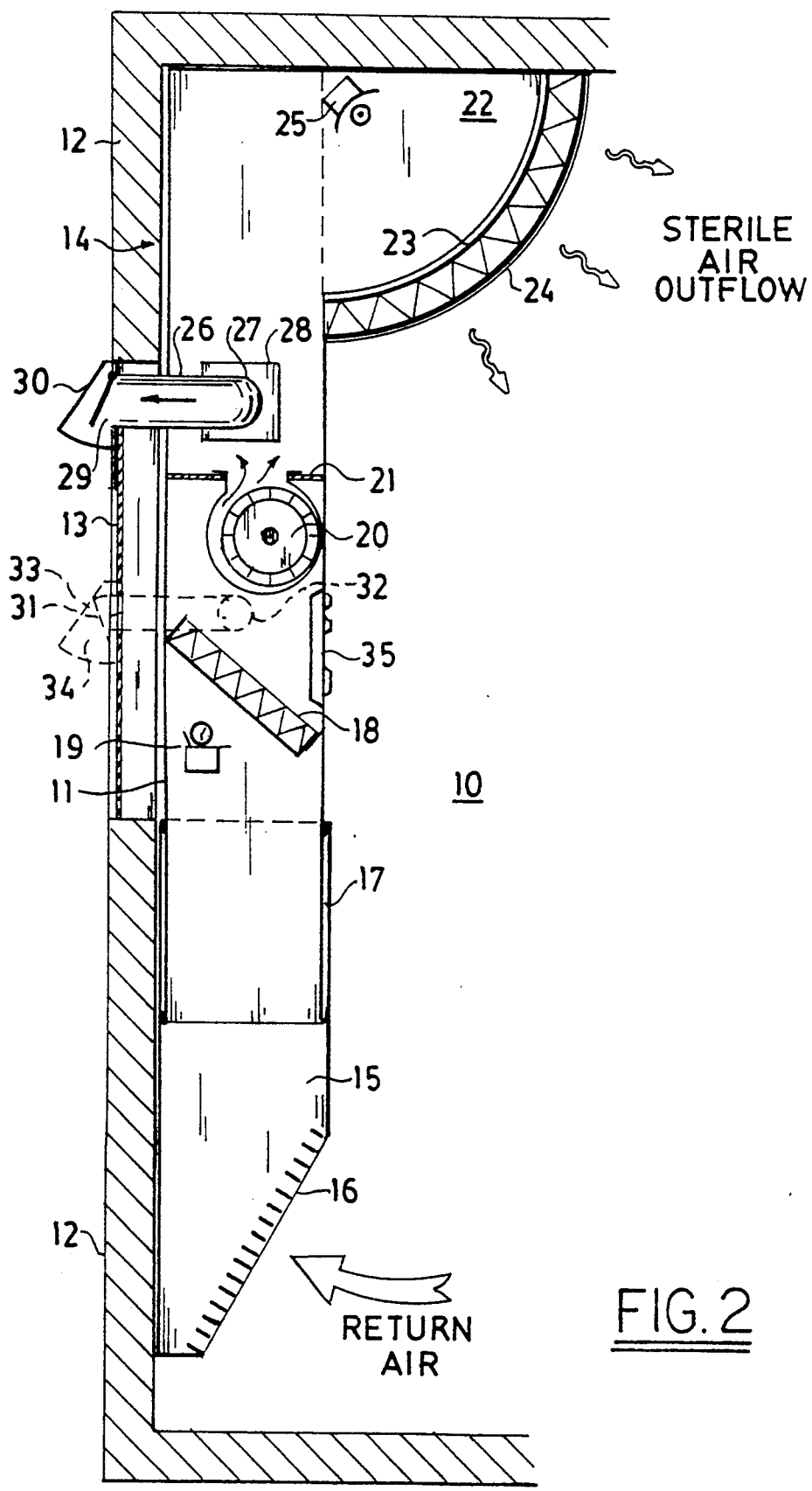
FIG. 2 is a side elevation of a room air sterilizer of FIG. 1.

With reference to FIGS. 1 and 2 of the Drawing, the room air sterilizer 10 according to this invention has an elongated vertical housing 11 of generally rectangular cross section mounted onto a wall 12 of a room. In this case, the sterilizer 10 is mounted near a window 13 or other wall penetration.

An upper end 14 of the housing is disposed against the room ceiling, while a lower end 15 is situated as near as possible to the floor of the room area. As shown here, there is beneath the lower end 15 sufficient clearance to permit cleaning the floor. In this embodiment, there is a return air grille 16 through which room air enters the lower end of the housing. However, in other possible embodiments, the housing could be coupled directly to a manifold within a false floor of the room.

An expandable sleeve portion 17 is allow the overall link of the housing 11 to be adjusted to fit the floor-to-ceiling distance of the room.

Within the housing and above the return air grill 16 is a prefilter 18 which removes coarse dust particles. Below the prefilter is an ultra-violet sterilizer lamp 19 which exposes the lower or intake surface of the prefilter 18 to ultraviolet light of about 254 nm. This serves to destroy any biocontamination on the particles that become lodged on the prefilter and permits the prefilter to be changed without need to gown up or take other extraordinary measures.

Above the prefilter 18 are one or more fans 20 disposed in a fan baffle 21 or steel diaphragm. These fans serve to draw the room return air in through the grill 16 and force it upwards to an outflow port 22 at the upper end 14 of the housing. In this embodiment, the room air sterilizer employs a pair of low noise centrifugal fans disposed in volute or snail-shell chambers. These fans together have an air moving capacity of about 300 cfm.

At the outflow port 22 is disposed a HEPA filter 23 through which sterile room supply air is exhausted into the room. In this case the filter 23 is a quarter cylinder arranged with its axis (i.e., its center of curvature) disposed horizontally and substantially at the level of the ceiling, so that the air that is exhausted through the filter moves outward and downward into the room. On the outside of the filter 23 there is a protective screen 24 in the form of a double-row of laths.

An ultraviolet sterilizer lamp 25 is disposed within the upper part 14 of the housing and is arranged to expose the entire inner surface, i.e. or inflow side, of the filter 23 to germicidal ultraviolet light. This light is preferably at a wavelength of about 254 nm. The HEPA filter 23 will trap airborne particulates and other particles down to a size of one micron or smaller, and the sterilizer lamp 25 will destroy any biocontamination on the particles that become lodged on the filter. The double-lath protective screen 24 permits free flow of air out through the filter 23, but obstructs the line of sight transmission of any of the ultraviolet radiation which might pass through the filter.

The relative room air pressure can be controlled, either to provide a slight overpressure or a slight underpressure relative to the room exterior, by means of dampers and ducts that are coupled to the housing 11.

For a negative relative pressure, an exhaust duct 26 is coupled at one end to an exhaust port in the housing which is situated between the fan baffle 21 and the outflow port 22. The other end of the duct 26 extends to the window 13 or other wall penetration. An optional HEPA filter 28 can be situated at the exhaust port 27, and serves the purpose of preventing contamination of the external air. As shown in FIG. 2, an exhaust balancing backdraft damper 29 is situated at the exhaust end of the duct at which a rainhood 30 is also provided. The exhaust duct 26 can also include manual dampers, which are not shown.

Alternatively, and as shown in ghost line, an intake duct 31 can be provided to achieve a positive pressurization or room overpressure. Here the intake duct 31 is coupled to an intake port 32 situated ahead of the fans 20, that is, at the intake side thereof. As shown in FIG. 2, the duct 31 extends to a rainhood 33 situated in the window 13, where an intake backdraft damper 34 is included to control the airflow through the duct. The arrows on the ducts 26 and 31 indicate the direction of airflow therethrough.

In this embodiment, there is a control panel 35 on the front of the housing 11. The control panel includes switches for the fan and for the lamps, as well as indicators to show functional status of the lamps 19 and 25 and also to indicate, for example, pressure drop across the filters 18 and 23. Additional indicators can be employed to show rate of air flow, particulate count, temperature, humidity and/or other quantities. The room air sterilizer 10 of this embodiment is a low power device and can plug into any standard wall outlet.

In alternative arrangements, instead of connecting the exhaust and or intake ducts 26, 31 through a window or other wall penetration, these can be coupled to a common manifold duct of the building ventilation system. Moreover, the lower end of the housing can extend to a manifold within a false floor of the room, rather than terminate above the floor. In that case, perforations in the false floor can permit a generally laminar airflow in the room, which can facilitate trapping of airborne particulate.

While the invention has been described in detail with respect to a preferred embodiment, it should be understood that the invention is not limited to that embodiment. Rather, many modifications and variations would present themselves to those skilled in the art without departing from the scope and spirit of this invention, as defined in the appended claims.

What is claimed is:

1. Room air sterilizer for filtering from air in a room particulates and aerosols and destroying microbial biocontamination thereon; comprising
    an elongated housing having an intake end with a return air port for drawing return air from near a floor of said room and a discharge end with an outflow port;
    blower means in said housing for blowing air from said return air port to said outflow port;
    a prefilter disposed in said housing before said blower means, said prefilter and said blower means defining a first reduced pressure zone within said housing;
    a HEPA filter assembly disposed at said outflow port for trapping and holding said particulates and aerosols as said air passes therethrough from an inflow side to an outflow side thereof, said HEPA filter assembly and said blower means defining a second increased pressure zone within said housing;
    a germicidal ultraviolet lamp disposed in said housing at its discharge end to expose the entire inflow side of said HEPA filter assembly to ultraviolet radiation at a wavelength suitable to destroy said microbial biocontamination;
    exhaust port means in said housing situated in communication with said second increased pressure zone to permit controlled ducting of air out therefrom;
    intake port means in said housing situated in communication with said first reduced pressure zone to permit addition of make-up air thereto;
    duct means connected to one of said exhaust port means and said intake port means for ducting exhaust air out of said room or make-up air into said housing from outside said room; and
    means for selectively controlling air flow through said duct means to permit the room air sterilizer to be selectively operated in an overpressure mode in which make-up air flows through said duct means and said intake port means into said first reduced pressure zone defined by said prefilter and said blower means to maintain a positive pressure within the room, or in an underpressure mode in which exhaust air flows from said second increased pressure zone defined by said blower means and said HEPA filter assembly through said exhaust port means and said duct means outside the room to maintain a negative pressure within the room.

2. Room air sterilizer according to claim 1 wherein said elongated housing includes a variable length duct extension to permit said return air port to be positioned adjacent the floor.

3. Room air sterilizer according to claim 1 further comprising a second germicidal ultraviolet lamp disposed below said prefilter to expose an inflow side thereof to ultraviolet radiation at said suitable wavelength.

4. Room air sterilizer according to claim 1 wherein said HEPA filter assembly includes a quarter-cylindrical filter, and said germicidal lamp includes a lamp tube disposed substantially at the axis of said quarter-cylindrical filter for maximally exposing the inflow side of said filter to the ultraviolet radiation.

5. Room air sterilizer according to claim 4 further comprising a protective screen formed of staggered rows of laths on the outflow side of said HEPA filter.

6. Room air sterilizer according to claim 1, said duct means comprising an exhaust duct coupled to said exhaust port means.

7. Room air sterilizer according to claim 6 wherein said exhaust duct includes an exhaust filter disposed at said exhaust port means.

8. Room air sterilizer according to claim 6 wherein exhaust duct includes a backdraft damper to check the flow of air through said exhaust duct.

9. Room air sterilizer according to claim 1, said duct means comprising an intake duct coupled to said intake port means.

10. Room air sterilizer according to claim 9 wherein said intake duct includes a backdraft damper to check and control the flow of air through said intake duct.

* * * * *